United States Patent
Yamaki et al.

(10) Patent No.: US 11,051,993 B2
(45) Date of Patent: Jul. 6, 2021

(54) TAMPON APPLICATOR

(71) Applicant: Unicharm Corporation, Shikokuchuo (JP)

(72) Inventors: Koichi Yamaki, Kanonji (JP); Akie Kinoshita, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 1153 days.

(21) Appl. No.: 15/300,274

(22) PCT Filed: Feb. 13, 2015

(86) PCT No.: PCT/JP2015/053949
§ 371 (c)(1),
(2) Date: Sep. 28, 2016

(87) PCT Pub. No.: WO2015/151602
PCT Pub. Date: Oct. 8, 2015

(65) Prior Publication Data
US 2017/0143557 A1    May 25, 2017

(30) Foreign Application Priority Data
Apr. 4, 2014  (JP) .............................. JP2014-077731

(51) Int. Cl.
*A61F 13/15* (2006.01)
*A61F 13/26* (2006.01)

(52) U.S. Cl.
CPC ............ *A61F 13/266* (2013.01); *A61F 13/26* (2013.01)

(58) Field of Classification Search
CPC ............................... A61F 13/26; A61F 13/266
See application file for complete search history.

(56) References Cited

U.S. PATENT DOCUMENTS

2004/0054317 A1* 3/2004 Lemay .................. A61F 13/266
                                                              604/15
2012/0101424 A1    4/2012 Watanabe

FOREIGN PATENT DOCUMENTS

JP        2012-5720 A       1/2012
WO      2007/115091 A1    10/2007
WO   WO-2010104166 A1 *   9/2010 ........... A61F 13/266

OTHER PUBLICATIONS

International Search Report in PCT/JP2015/053949, dated Apr. 28, 2015.

* cited by examiner

*Primary Examiner* — Bradley H Philips
(74) *Attorney, Agent, or Firm* — Hauptman Ham, LLP (57) ABSTRACT

The present invention provides an applicator improved so that the entirety of the tampon may be reliably inserted into vagina.
A raised portion is located on an exterior surface of an inner tube in the vicinity of a rear end thereof and put in a slidable contact with a part of an interior surface of an outer tube. The raised portion has an outer shape having a width dimension gradually increasing rearward from an apex located on a front end.

5 Claims, 10 Drawing Sheets

TAMPON APPLICATOR

RELATED APPLICATIONS

This application is a National Stage of PCT international application Ser. No. PCT/JP2015/053949, filed on Feb. 13, 2015, which claims priority to Japanese Patent Application No. 2014-077731, filed on Apr. 4, 2014.

TECHNICAL FIELD

The present invention relates to a tampon applicator used to insert a tampon into the vagina.

BACKGROUND

Various types of applicators used to insert tampons into the vagina are known. For example, an applicator disclosed in PTL 1 (p.s.) has an outer tube to house a tampon therein and an inner tube partially located inside the outer tube and used to eject the tampon from the outer tube. On the exterior surface of the inner tube, two or more raised areas are arranged so that the raised portions may be latched by a latching part on the interior surface of the outer tube in ejecting the tampon from the outer tube.

CITATION LIST

Patent Literature

{PTL 1}: WO 2007-115091 A1

SUMMARY

Technical Problem

In the applicator according to the invention disclosed in PTL 1, when the rear end of the inner tube is pushed to push out the tampon's main body, the exterior surface of the inner tube slidably contacts with the interior surface of the outer tube and a protrusion formed on the exterior surface is engaged with the latching portion formed on the interior surface. This prevents the inner tube from dropping out. In addition, click feeling generated when the protrusion is latched enables the user to make sure that the tampon has been inserted into the vagina.

However, in such arrangement, relatively large pressing force is required to latch the protrusion on the latching portion and, upon generation of such large pressing force, the user is often misled into thinking that the tampon has completely inserted into the vagina and may stop the pushing operation before the tampon is completely ejected from the outer tube.

An object of the present invention is to improve the conventional tampon applicator so that the entirety of the tampon may be more reliably inserted into the vagina.

Solution to Problem

To solve the problem as has been described above, the present invention is directed to an tampon applicator comprising an outer tube having a front end and a rear end, openings at the front and rear ends, and an inner tube configured to be inserted into the outer tube from the rear end opening slidable in a front-back direction, thereby ejecting a tampon housed within the outer tube through the front end opening.

The present invention is featured in the tampon applicator that a raised portion is disposed on an exterior surface of the inner tube adjacent to the rear end thereof configured to be put in slidable contact with an interior surface of the outer tube when the front end of the inner tube moves to the front end of the exterior tube; and the raised portion has a front end, a front zone having a nearly V-shape with a width dimension gradually increasing from the apex of the front end rearward and a rear zone located behind the front zone having a width dimension gradually decreasing rearward.

Advantageous Effects of Invention

In one or more embodiments of the tampon applicator according to the present invention, the raised portion configured to be put in slidable contact with the interior surface of the outer tube is arranged on the exterior surface of the inner tube adjoining the rear end thereof. The raised portion has an outer shape having a width dimension gradually increasing from the apex toward the rear as the inner tube moves forward, in other words, an area over which the raised portion and the outer tube are put in slidable contact increases in the direction in which the inner tube is inserted and the frictional resistance due to such contact gradually increases. In consequence, it is possible for the user to recognize sensuously the state right before the insertion of the tampon is completed but to recognize that the operation of insertion is not completed. Since the frictional resistance gradually increases, the user continues to ejection operation until the tampon is reliably inserted into the vagina.

BRIEF DESCRIPTION OF DRAWINGS

The drawings illustrate specific embodiments of the present invention including optional and preferred features as well as essential features of the invention.

DESCRIPTION OF EMBODIMENTS

The embodiments described below relate to a tampon applicator illustrated in FIGS. 1 through 10, including both optional and preferred features as well as those features which are essential features of the present invention.

Figure 1:
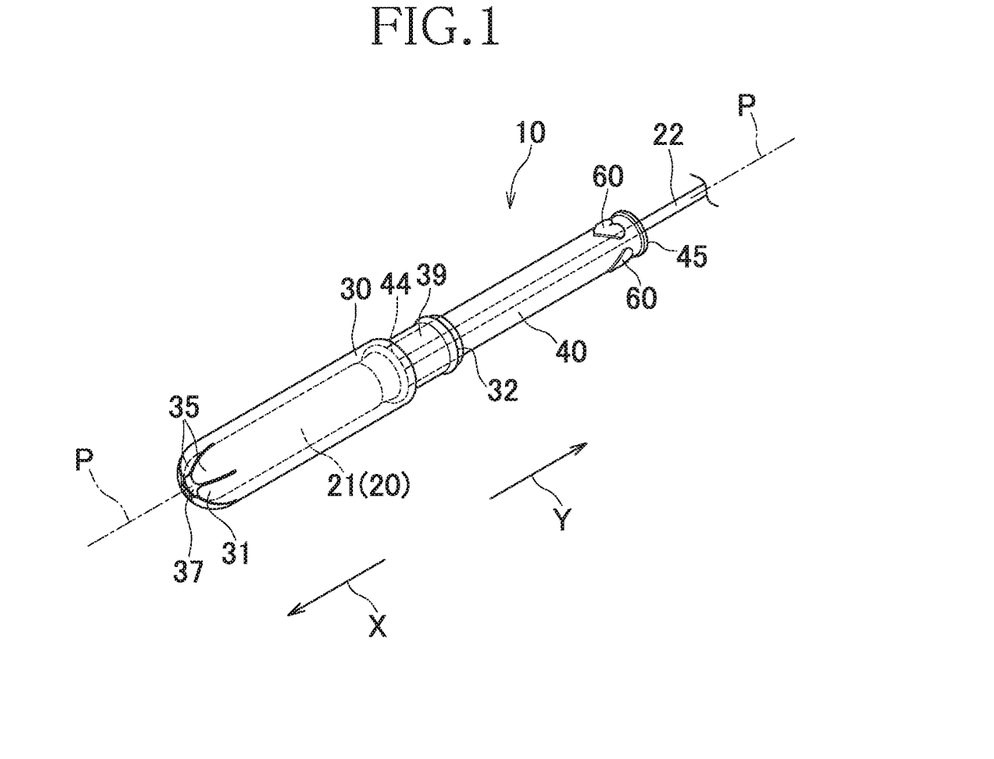
FIG. 1 Perspective view of a tampon applicator according to the present invention.
Figure 2:
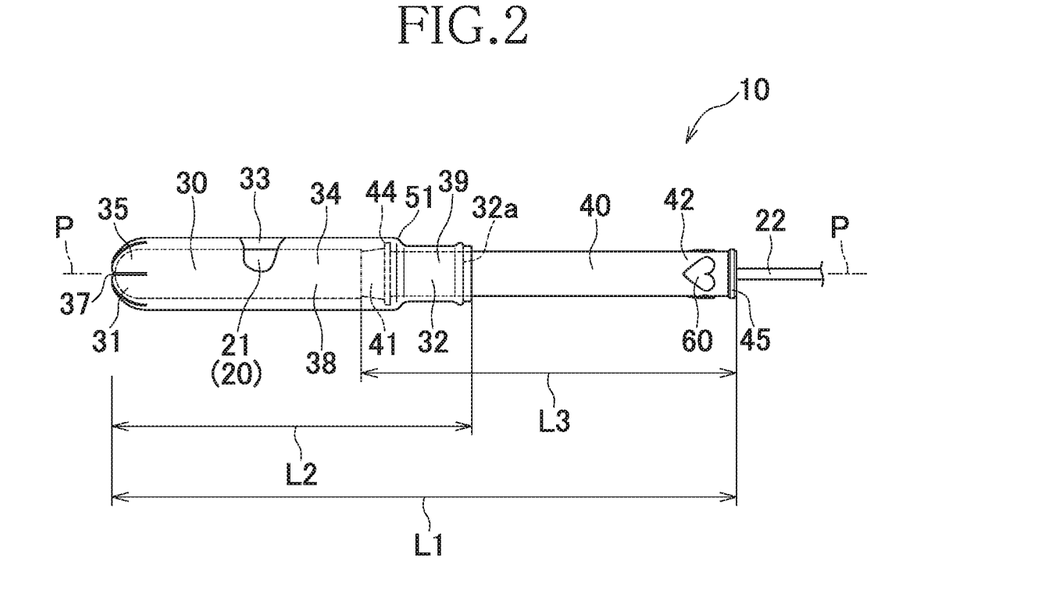
FIG. 2 Lateral view of the applicator.

Referring by way of example to FIGS. 1 and 2, a tampon applicator 10 according to the present invention has a generally cylindrical shape and includes a central axis P, an outer tube 30 to house a tampon 20, and an inner cylinder 40 configured to be telescoped into the outer cylinder 30 thereby to eject an absorbent body 21 of the tampon from the outer cylinder 30. The inner cylinder 40 has a cylindrical shape having a diameter smaller than that of the outer cylinder 30, and includes a withdrawal cord 22 extending rearward from a rear end of the absorbent body 21 through inner tube 40.

The outer cylinder 30 has front and rear ends 31, 32 spaced from each other and opposed to each other in the longitudinal direction and interior and exterior surfaces 33, 34. On the front end 31, an ejection opening 37 is defined by two or more petals 35 configured to open out under elastic deformation when the tampon 20 is ejected. On the rear end 32, a rear end 32a is located, through which the inner tube 40 is telescoped so that the inner tube 40 may be slidable to a front direction X and a rear direction Y. The petals 35 are tapered toward the central axis P.

The outer tube 30 has, in addition, an insertion section 38 defined on the side of the front end 31 with a relatively larger diameter and a grip section 39 extending to the rear direction Y from the insertion section 38 with a relatively smaller diameter. Along a boundary between the insertion section 38 and the grip section 39, a shoulder portion 51 is located to prevent falling off of the inner tube 40 from the outer tube 30. The insertion section 38 slidably stores therein the absorbent body 21 shaped in a rod having circular or square cross section. Though not illustrated, it is possible to arrange a plurality of protrusions extending in a circumferential direction on the exterior surface of the grip section 39 as antislip or reinforcing means functioning when the grip section 39 is held.

Figure 3A:
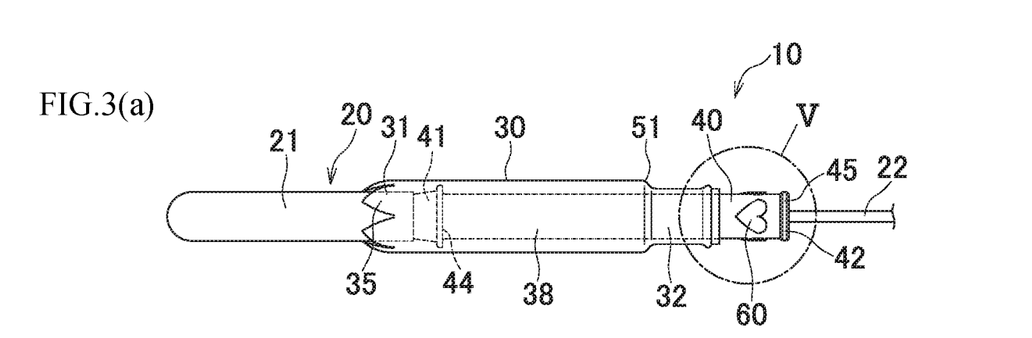
FIG. 3(a) Lateral view illustrating a state in which a tampon has been partially ejected by an inner tube through an opening of an outer tube.
Figure 4:
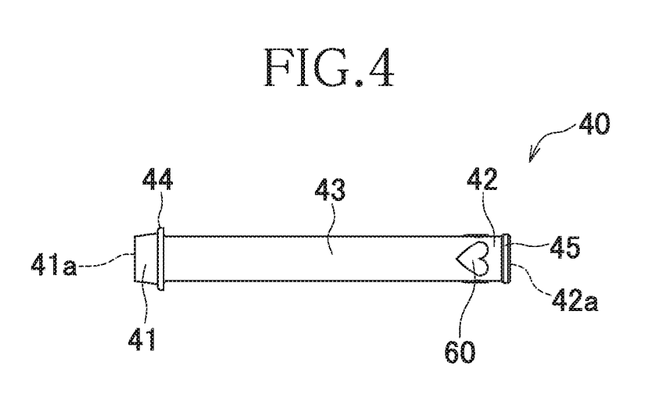
FIG. 4 Lateral view of the inner tube.

Referring by way of example to FIGS. 2 through 4, the inner tube 40 is opened at both ends thereof and has front and rear ends 41, 42 spaced from and opposed to each other and exterior surfaces 43 thereof. The front and rear ends 41, 42 respectively have front and rear end openings 41a, 42a through which the withdrawal cord 22 extends wherein these exterior surfaces 43 respectively have front and rear flanges 44, 45 protruding outward therefrom. The front flange 44 is located so as to be slightly spaced apart from the front end opening 41a to the rear direction Y and the rear flange 45 is located at a circumferential edge of the rear end opening 42a. On the exterior surface 43 of the inner tube 40 adjacent to the rear end 42, two or more raised portions 60 are located so as to be spaced apart from each other in the circumferential direction. The front end 41 of the inner tube 40 is slightly tapered from the front flange 44 toward the front end opening 41a and abut against a rear end surface of the absorbent body 21.

The inner tube 40 and the outer tube 30 may be obtained by using known polyolefin thermoplastic resins of polyolefin-series such as polyethylene or polypropylene and injection-molding such resins. Specifically, the outer tube 30 is preferably molded from a flexible material which facilitates the petals 35 in bud-state to open when the tampon 20 is ejected through the ejection opening 37. Flexibility of the inner tube 40 necessary for elastic deformation of the raised portions 60 of the inner tube 40 is preferably comparable to or lower than that of the outer tube 30 for smooth ejection of the tampon 20 so long as a required strength of the inner tube 40 is assured. The insertion section 38 of the outer tube 30 has a hollow interior volume to house the tampon 20 and a diameter of such hollow interior volume ranges from about 10 mm to about 25 mm. A diameter of the inner tube 40 is smaller than that of the outer tube 30 and an outer diameter of the front flange 44 is larger than an inner diameter of the grip section 39 so that the front flange 44 is engaged with the shoulder portion 51 in pulling the inner tube 40 to the rear direction Y, thereby further movement thereof to the rear direction Y is restricted and pulling out of the inner tube 40 from the rear end opening 32a is prevented. In this regard, the flexibility of the inner tube 40 may be lower than that of the outer tube 30 so long as the raised portions 60 have the desired function.

Referring by way of example to FIG. 2, the maximum length dimension L1 of the applicator 10 in its assembled state (in a state that the inner tube 40 has been pulled to the rear direction Y until the front flange 44 comes in contact with shoulder portion 51 ranges from about 80 mm to about 130 mm, a length dimension L2 of the outer tube 30 ranges from about 50 mm to about 80 mm and a length dimension L3 of the inner tube 40 is substantially the same to or slightly smaller than the length dimension L2 of the outer tube 30, specifically, ranging from about 40 mm to about 70 mm. A diameter of the tampon 20 ranges from about 8.0 mm to about 12.0 mm. These dimensions as mentioned above are preferable for the respective tubes.

The inner tube 40 and the outer tube 30 have approximately the same length dimensions so that the rear end edge of the inner tube 40 nearly coincides with the rear end edge of the outer tube 30 when the front end 41 of the inner tube 40 has been pushed forward enough to open up the petals 35 located on the front end 31 of the outer tube 30. As previously described, the maximum outer diameter of the inner tube 40 (i.e., the outer diameter of the front flange 44) and the outer diameter of the absorbent body 21 are smaller than the inner diameter of the insertion section 38 so that, when the absorbent body 21 is ejected by the inner tube 40, the absorbent body 21 slidably moves together with inner tube 40 within the outer tube 30, and when the tampon 20 make it possible to insert the tampon 20 smoothly into the vagina.

Figure 3B:
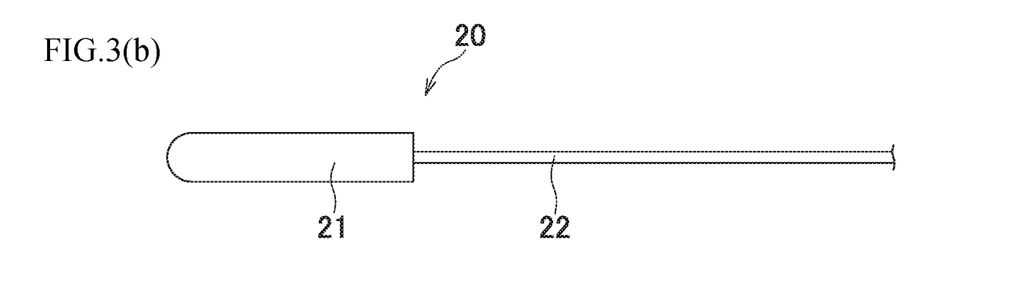
FIG. 3(b) Lateral view of the tampon.

Referring by way of example to FIG. 3(b), the tampon 20 includes the absorbent body 21 and the withdrawal cord 22 extending rearward from the absorbent body 21. The absorbent body 21 is a rod-like element obtained by compression-molding absorbent materials commonly used for bodily-fluid absorptive articles, for example, natural fibers such as cotton or pulp, or recycled or semisynthetic fibers such as rayon or acetate fibers, and may optionally contain nonwoven fabrics, tissue papers and foamed plastic. It is also possible to use fibrous nonwoven fabrics of rayon-cotton mixture processed to have a rolled shape. The withdrawal cord 22 for the tampon 22 is formed of synthetic fibers such as nylon or polyester or natural fibers and has a tensile strength at a degree ensuring that the absorbent body 21 located in the vagina and having absorbed the bodily fluid may be safely withdrawn. Specifically, it is preferred to use the material for the withdrawal cord 22 having a tensile strength of about 5 N or higher enough to avoid an accidental cutoff during withdrawal of the tampon 21 and, in addition, being free from a tendency of generating capillary action.

Figure 5:
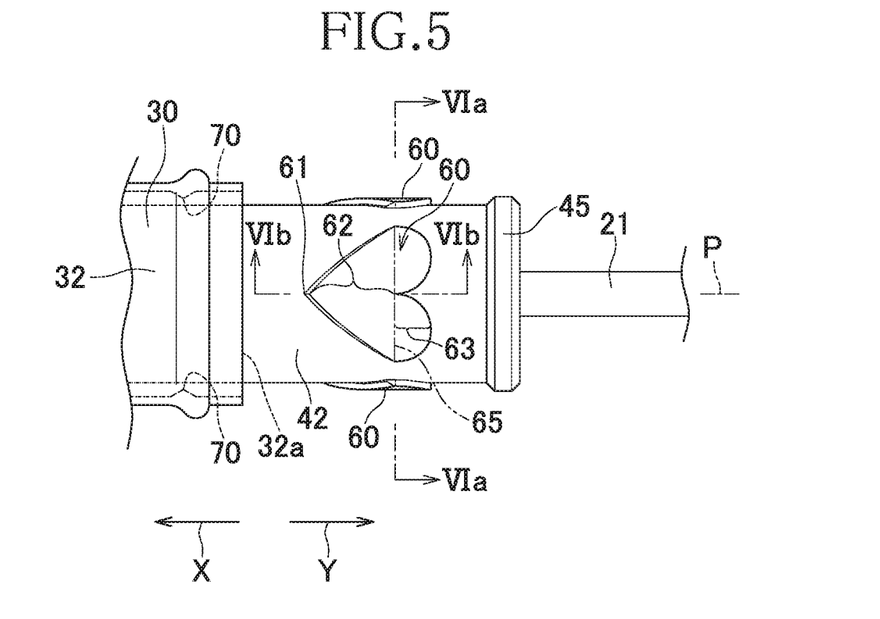
FIG. 5 Scale-enlarged diagram of a portion surrounded by a circular line V in FIG. 3.
Figure 6A:
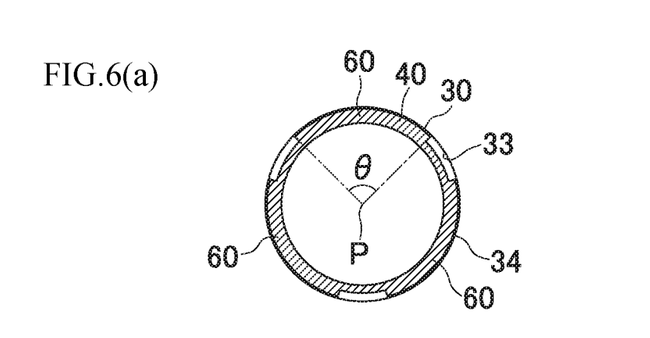
FIG. 6(a) Sectional end view taken along line VIa-VIa in FIG. 5.
Figure 6B:
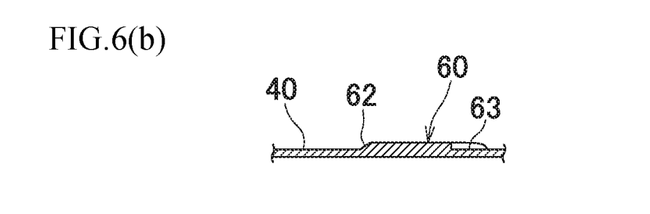
FIG. 6(b) Sectional end view taken along line VIb-VIb in FIG. 5.

Referring by way of example to FIG. 5, each of the raised portions 60 on the inner tube 40 has a contour shape gradually widening from the front end toward the rear end substantially to define a heart-shape, one of the axisymmetric shapes. The raised portion 60 has an apex 61 on the front end, a front portion 62 having a generally V-shaped contour extending rearward at a slant from the apex 61 and a rear portion 63 having two circular arc zones which extend in the rear direction Y from the front portion 62. In FIG. 5, a boundary between the front portion 62 and the rear portion 63 is indicated by an imaginary line 65. Referring to FIG. 6(a), the two or more raised portions 60 being the same in size and form are arranged at regular intervals in the circumferential direction on the exterior surface of the inner tube 40. In the present embodiment, three raised portions 60 are arranged at regular intervals in the circumferential direction and on the same position as viewed in the front-back direction so that these raised portions 60 simultaneously come in contact with the interior surface 33 (specifically, a protrusion 70 described later), thereby the frictional resistance is dispersed, making it possible to move the inner tube 40 to the front direction X and the rear direction Y without decentering the inner tube 40. A center angle θ around the central axis P in each of the raised portions 60 ranges from about 70° to about 100°. Referring to FIG. 6(b), the front portion 62 of the raised portion 60 is shaped so as to be slightly sloped so that a height (thickness) dimension thereof may increase (thicken) from the front portion to the rear portion.

The grip section 39 of the outer tube 30 is shaped so as to extend radially outward at a diameter enlarged portion defined around the edge of the rear end opening 32a and to have the protrusion 70 extending from the interior surface 33 of the opening's outer tube 30 toward the central axis P wherein the interior surface 33 of the outer tube 30 narrowing from the rear direction Y to the front direction X. The outer diameter of the inner tube 40 at the raised portions 60 is nearly the same as or slightly larger than the outer diameter at the protrusion 70 so that the respective raised portions 60 may slidably contact with the protrusion 70 under elastic deformation and generate frictional resistance. In this regard, it is also possible to ensure forward movement of the inner tube 40 under the elastic deformation of the respective raised portions 60 as the protrusion 70 of the outer tube 30 slidably contact with the respective raised portions 60 of the inner tube 40 or to form the outer tube 30 from the material having a stiffness higher than that of the inner tube 40 so that the protrusion 70 may be elastically deformed.

Figure 7:
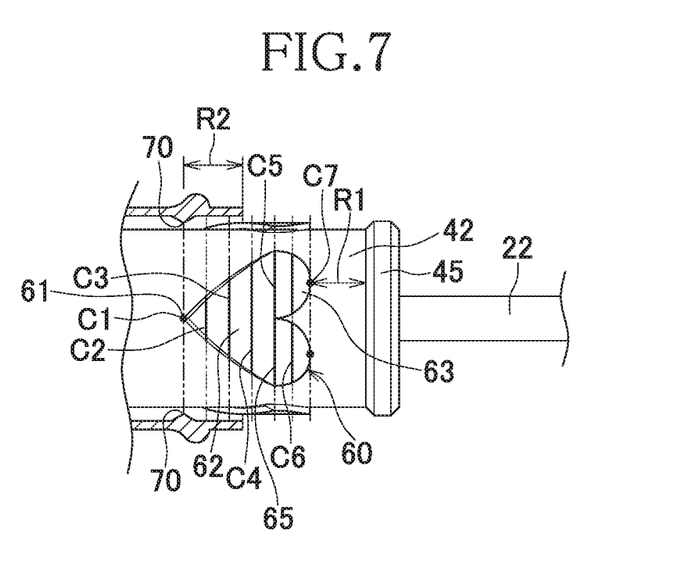
FIG. 7 Scale-enlarged diagram similar to FIG. 5, wherein raised portions on the inner tube about a protrusion on the outer tube.

Referring by way of example to FIG. 7, the raised portion 60 is shaped so that the front zone 62 has a width dimension gradually increased from the apex 61 rearward and consequently an area put in contact with the protrusion 70 gradually increases as the raised portion moves to the front direction X. In other words, contact areas C1 through C5 enlarged as the inner tube 40 is moved to the front direction X and consequently the frictional resistance gradually increases. Specifically, the contact area C1 defined between the protrusion 70 and the raised portion 60 at the apex 61 is point-like and the frictional resistance of a degree which is feelable for the user is not generated at this contact area C1 (i.e., frictional resistance≈0). As the inner tube 40 further moves to the front direction X after the apex 61 has moved past the protrusion 70, the contact area gradually increases in the order of the contact areas C2 through C5 until the maximum contact area C5 defined by a position at which the protrusion 70 rides a branching point of the rear end edge, i.e., the boundary 65 between the front zone 62 and the rear zone 63. As the inner tube 40 is further moved toward the front direction X, the contact area gradually decreases because the rear zone 63 has the width dimension (or the surface area) gradually decreasing rearward and has a bifurcated contour. More specifically, a contact area C6 defined nearly to the maximum contact area C5 has a planar dimension and a frictional resistance both being less than in the maximum contact area C5 and a contact area C7 defined nearly to the contact area C6 has a planar dimension and a frictional resistance both being less than in the contact area C6. The raised portion 60 slidably contacts locally with the protrusion 70 as a portion of the interior surface 33 of the outer tube 30 so as to define a linear contact area extending in a circumferential direction so that the contact area and the friction resistance depending thereupon may be restricted in comparison with when the raised portion 60 is put in contact with the outer tube 30 in planar fashion.

In the present embodiment, as previously described, the exterior edge of the front zone 62 in the raised portion 60 is sloped so that the height dimension may gradually increase from the front toward the rear and the raised portion 60 may be smoothly put in slidable contact with the protrusion 70 the front zone 62 should not be caught or broken in the slidable contact. The raised portion 60 is located at a given distance toward the front direction X from the rear flange 45 of the inner tube 40. Such placement of the raised portion 60 at a given distance from the rear flange 45 ensures that, when the raised portion 60 completely overpasses the protrusion 70 in moving forward in the font direction X under slidable contact with the protrusion 70, the raised portion 60 and the protrusion 70 become out of contact with each other and no frictional resistance is generated therebetween. Thus, it is possible for the user to make sure that a large part or entirety of the tampon 20 has been safely inserted into her vagina.

Specifically, a distance dimension RI between the rear flange 45 and the rear zone 63 of the raised portion 60 preferably ranges from about 1.5 mm to about 3.0 mm in order to ensure advantageous effects of the present invention as described more in details. In other words, the distance dimension RI preferably corresponds to a dimension represented by [a distance dimension RI between the protrusion 70 and the opening end edge of the outer tube 30+about 0.5 mm or more]. The distance dimension RI as specified above is preferable for the reason that, after the protrusion 70 has been completely out of contact with the raised portion 60, the inner tube 40 may be moved forward until the opening end edge of the rear end opening 32a comes in contact with the rear flange 45 of the inner tube 40 and finally interfitting of the inner and outer tubes 30, 40 may be surely sensed. Contrariwise, if a difference between the distance dimension R1 and the distance dimension R2 is about 0.5 mm or less, the opening end edge and the rear flange 45 come in contact with each other almost simultaneously when the level of frictional resistance becomes zero wherein it might be difficult to get feel reliably complete interfitting of the inner and outer tubes 30, 40 in a convincing way.

Figure 8:
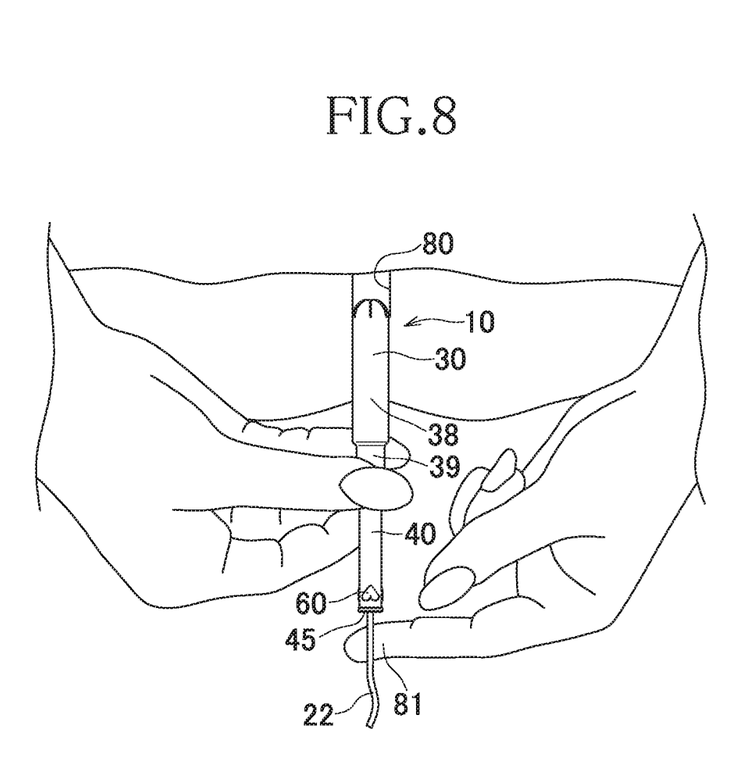
FIG. 8 Schematic diagram exemplarily illustrating a step during use of the applicator.

Referring by way of example to FIGS. 7 and 8, as an example of the method to insert the tampon 20 in a vagina 80 using the applicator, the front end portion of the applicator 10 held by one hand into the vagina 80 and the rear end 42 of the inner tube 40 is pushed with the forefinger of the other hand to move the inner tube 40 to the front direction X (toward the side of the vagina 80). With such method, it is impossible for the user to make sure visually that the tampon 20 has been properly inserted into the vagina.

During such operation of insertion, the rear end 42 of the inner tube 40 may be pushed toward the front direction X so as to eject the tampon 20 through the ejection opening 37. In this manner, it is possible to move the inner tube 40 smoothly without generation of the frictional resistance for the reason that both the tampon 20 and the inner tube 40 are kept from contact with the interior surface 33 of the outer tube 30. In further pushing operation, when the front flange 44 of the inner tube 40 reaches the front end 31 of the outer tube 30, the most part of the absorbent body 21 is inserted in the vagina 80 and the raised portion 60 of the inner tube 40 is put in slidable contact with the protrusion 70 of the outer tube 30.

A frictional resistance is generated owing to such slidable contact between the raised portion 60 and the protrusion 70 and the user is required to push the inner tube 40 by further strong force. The raised portion 60 is shaped so that the surface area thereof gradually increases rearward and, for this reason, the user is required to push the inner tube 40 by gradually increasing force. Thereafter, the user may continue to push the inner tube 40 until the raised portion 60 completely overpasses the protrusion 70 and, when any level of the frictional resistance is no more generated, it is possible for the user to recognize that the tampon 20 has been surely inserted into the vagina 80. The user pushes the inner tube 40 only with the forefinger 81, thereby ejects the tampon 20 only with the forefinger 81 so that even slight increase and decrease may be sensuously recognized.

For the exterior surface of the inner tube having none of the raised portions (including the raised portion having a locking function, in some situations), no frictional resistance is generated in pushing the inner tube and, for this reason, it is impossible for the user to make sure that the tampon has been fully inserted into the vagina. Besides, for the raised portion shaped so as to have no variation in the surface area thereof, it is possible for the user to predict completion of the tampon insertion immediately prior thereto on the basis of the frictional resistance generated at a moment of slidable contact between the raised portion and the protrusion. However, no change appears in the frictional resistance level even if the user continues to move the inner tube forward and, for this reason, some of the users might erroneously consider that the tampon has been fully inserted into the vagina and stop the ejection operation before the tampon is ejected through the ejection opening. Also when the user failed to catch the moment at which a frictional resistance was generated as the raised portion was put in a slidable contact with the interior surface of the outer tube, it is impossible for such user to capture the moment at which the tampon ejection operation is completed. If the applicator is withdrawn from the vagina before the tampon is completely ejected through the ejection opening, the tampon will not be properly inserted and the tampon might fall off from the vagina and/or menstrual blood might be not absorbed by the tampon but leak out.

The frictional resistance generated by the raised portion 60 according to the present invention functions as an advanced sign to inform the user with completion of tampon inserting operation immediately prior thereto and simultaneously functions as a continuation sign until the tampon 20 is fully ejected. Specifically, generation of the frictional resistance informs the user with a situation immediately before the operation for insertion of the tampon 20 is completed. Meanwhile, the frictional resistance is gradually increased as the inner tube 40 is moved forward and the insertion of the absorbent body 21 is not completed so long as the frictional resistance is increasing or decreasing. In consequence, the user continues to pushing operation and the user should not consciously stop the pushing operation. The user continues to push the inner tube until the frictional resistance disappears and it is possible for the user to make sure that the operation of insertion was completed only after the raised portion 60 had finally overpassed the protrusion 70 and frictional resistance of any level had been generated any more. Even if the inner tube 40 is further pushed forward until the rear flange 45 is moved into the rear end opening 32a of the outer tube 30, the front end 41 of the inner tube 40 collides with the inner surface of the front end 31 of the outer tube 30 and elastically rebounds for the reason that the petals 35 forming the front end 31 of the outer tube 30 have elasticity. When the user's forefinger 81 is released from the inner tube 40, the rear flange 45 projects to the rear direction Y from the rear end 32 of the outer tube 30.

When the front zone 62 of the raised portion 60 has an arc-like shape or a shape linearly extending in the circumferential direction of the inner tube 40, the surface area of the front zone 62 does not gradually increase toward the rear direction Y and it is difficult to change the frictional resistance value in a stepwise fashion at a degree recognizable for the user. However, the raised portion 60 comes in contact with the protrusion 70, at the apex 61 located on the front direction X and substantially no frictional resistance is generated in this step. Starting from the state substantially free from frictional resistance, it is possible to change the frictional resistance value gradually at a degree of sharpness which is recognizable by the user even when a dimension of the raised portion 60 in front-back direction is relatively small.

The raised portion 60 is shaped so that a width dimension thereof gradually decreased from the contact area C5 of the front zone 62, in which the friction resistance becomes the maximum value (peak value), toward the rear, and the frictional resistance is gradually decreased in the rear zone 63. Consequently, the user may push the inner tube 40 forward until the frictional resistance reaches the peak value and, on the basis of the frictional resistance decreasing, may recognize completion of the insertion operation (disappearance of the frictional resistance) immediately prior to the completion. It is also possible to form the raised portion 60 not on the exterior surface 43 of the inner tube 40 but on the interior surface 33 of the outer tube 30 so as to be put in slidable contact with a portion of the flat exterior surface 43 of the inner tube 40 so long as the advantageous effects of the present invention is ensured. Besides, after the tampon 20 has been inserted into the vagina, it is also possible to lock the raised portion 60 by a locking part formed on the interior surface 33 of the outer tube 30 to restrict the movement of the inner tube 4 in the raised portion 60.

Though it is possible to obtain the technical effects also when the raised portion 60 is on the interior surface 33 of the outer tube 30, the raised portion on the exterior surface 43 of the inner tube 40 enables the user to recognize the raised portion 60 visually prior to use and in wearing operation and to know that the applicator has the sign function informing the user with completion of the tampon insertion immediately prior to the completion. Stereoscopic shape or pattern having a design effect such as heart-shape may be employed to improve an ornamental design effect and to create an impression upon the user. In addition, it is effective to print a description of the sign functions on package paper for the applicator 10.

<Measurement of (the Maximum) Frictional Resistance Values>

TABLE 1 in the next paragraph indicates the maximum frictional resistance value (N) generated in an embodiment of the applicator according to the present invention and the maximum frictional resistance value (N) generated in a comparative example which is similar to the embodiment in the basis arrangement but different from the embodiment only in the shape of the raised portions when the inner tube 40 was moved forward until the raised portions 60 come in slidable contact with the protrusion 70. FIG. 9(*a*) is a diagram similar to FIG. 5, illustrating a configuration of the raised portions in the comparative example 1 during measurement of the maximum frictional resistance, FIG. 9(*b*) is a schematic cross-sectional view taken along line IXb-IXb in FIG. 9(*a*), FIG. 9(*c*) is a diagram similar to FIG. 5, illustrating a configuration of the raised portions in the comparative example 2 during measurement of the maximum frictional resistance and FIG. 9(*d*) is a schematic cross-sectional view taken along line IXd-IXd in FIG. 9(*c*).

TABLE 1

| | maximum frictional resistance (N) | cases of ejection action stopped in mid-course (%) |
|---|---|---|
| Embodiment | 1 | 3.5% |
| Comparative Example 1 | 2.7 | 18.0% |
| Comparative Example 2 | 3.5 | 32.0% |

Embodiment

Each of the raised portions 60 in the applicator 10 according to Embodiment is nearly heart-shaped and totally three raised portions 60 are arranged at regular intervals on the exterior surface of the inner tube 40. In each of the raised portions 60, the height dimension of the rear zone 63 (the zone having the largest height dimension) is about 0.25 mm, a central angle θ around the central axis P is approximately 100° and a distance dimension R1 between the raised portion 60 and the rear flange 45 is about 3.74 mm.

Comparative Example 1

Figure 9A:
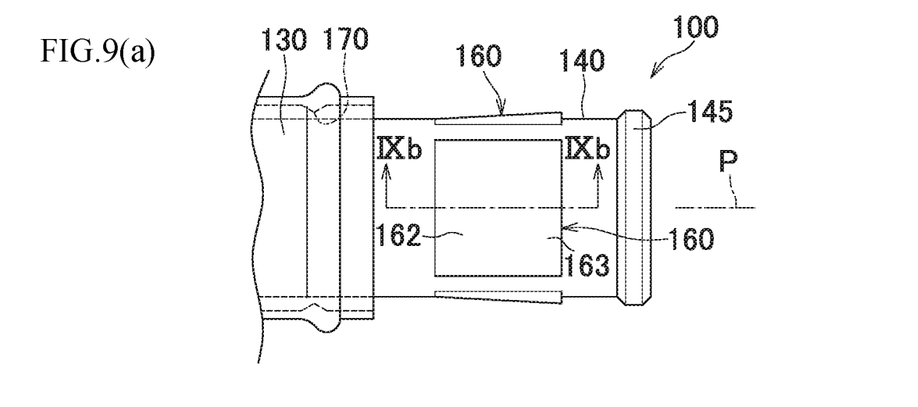
FIG. 9(a) Lateral view illustrating a form of the raised portion in comparative example 1 in measuring the maximum friction resistance value.
Figure 9B:
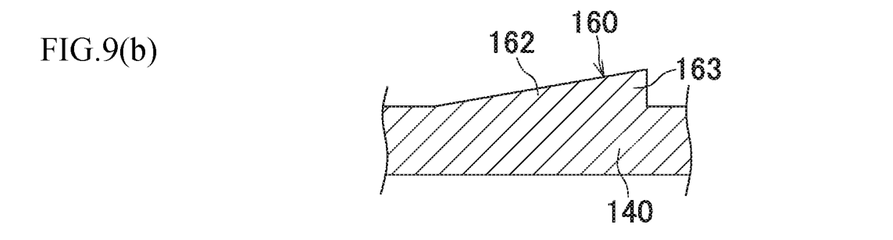
FIG. 9(b) Partial cross-sectional view taken along line IXb-IXb in FIG. 9 (a).

In the applicator 100 according to Comparative Example 1, totally three raised portions 160 are arranged at regular intervals on the exterior surface of the inner tube 140 and in each of the raised portions 160, the height dimension of the rear zone (the zone having the largest height dimension) 163 is about 0.25 mm, the central angle θ around the central axis P is approximately 100° and the distance dimension R1 between the raised portion 160 and the rear flange 145 is about 3.74 mm. Referring to FIG. 9(*a*), the raised portion 160 in the comparative example 1 is different from the embodiment in that the raised portion 160 is nearly rectangular and the front zone 162 has the same width dimension as that of the rear zone 163.

Comparative Example 2

Figure 9C:
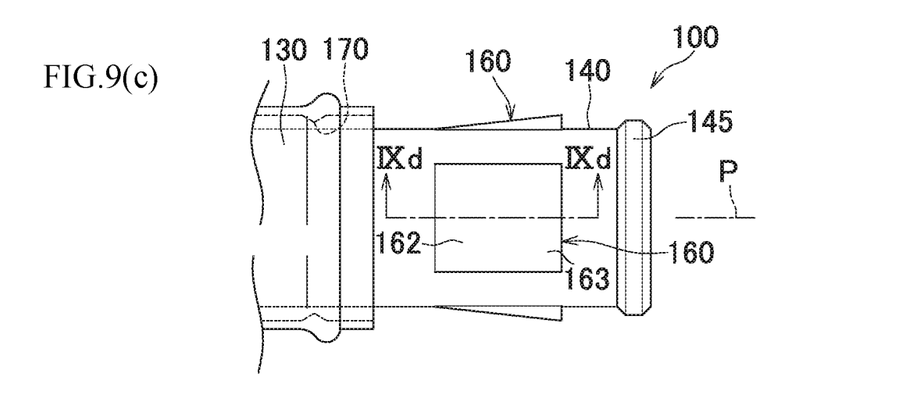
FIG. 9(c) Lateral view illustrating a form of the raised portion in comparative example 2 in measuring the maximum friction resistance value.
Figure 9D:
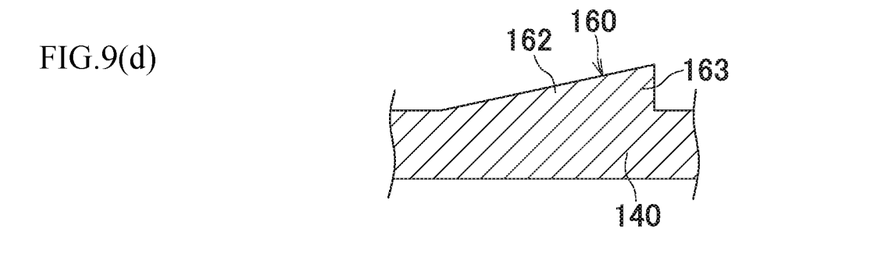
FIG. 9(d) Partial cross-sectional view taken along line IXd-IXd in FIG. 9 (c).
Figure 10A:
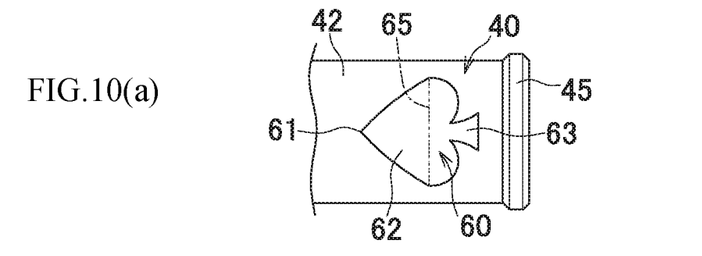
FIG. 10(a) through FIG. 10(e) Scale-enlarged lateral views of the raised portions exemplarily illustrating alternatives of the applicator.
Figure 10B:
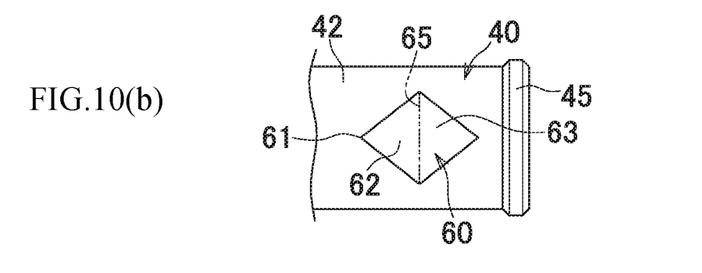
Figure 10C:
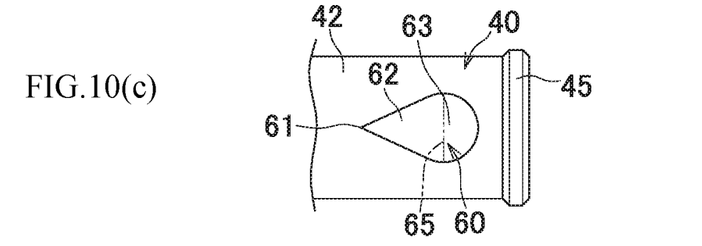
Figure 10D:
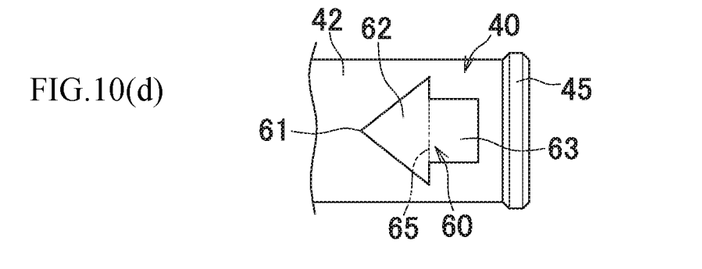
Figure 10E:
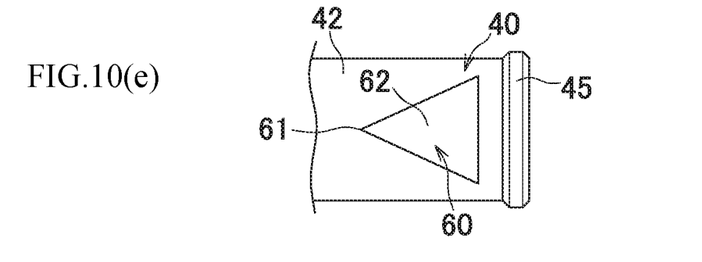

In the applicator 100 according to Comparative Example 2, totally three raised portions 160 are arranged at regular intervals on the exterior surface of the inner tube 140 and in each of the raised portions 160, the height dimension of the rear zone (the zone having the largest height dimension) 163 is about 0.3 mm, the central angle θ around the central axis P is approximately 75° and the distance dimension R1 between the raised portion 160 and the rear flange 145 is about 3.74 mm. Referring to FIG. 9(*c*), the raised portion 160 in the comparative example 1 is different from the embodiment in that the raised portion 160 is nearly rectangular and the front zone 162 has the same width dimension as that of the rear zone 163.

<Measuring Method>

For measurement of the maximum frictional resistance in Embodiment and Comparative Examples 1, 2, Compression Tester (Precision Universal Testing Machine "AUTOGRAPH AG-1) manufactured by Shimadzu Corporation was used. The inner tube 40 was inserted into the outer tube 30 still not containing the tampon 20, then the insertion section 38 was clamped and the rear end 42 of the inner tube 40 was pushed at a constant rate of about 100 mm/min with the upper chuck (with the lower chuck being detached). The inner tube 40 was moved forward within the outer tube 30 and a frictional resistance value (compression value) generating due to slidable contact between the raised portion 60 and the protrusion 70 (C1 in FIG. 7) was continuously measured until the raised portion 60 completely passed over the protrusion 70, any frictional resistance is no more generated, the front end of the inner tube 40 reaches the front end 31 of the outer tube 30 and ejected through the ejection opening 37 and the maximum value of the frictional resistance values measured in this manner was recorded as the maximum frictional resistance value. In addition, a measurement was made 10 times on the Embodiment and the Comparative Examples 1 and 2, respectively to 10 females (in the ages of 20 s to 40 s) having experience of using tampon applicators wherein the rear end of the inner tube 40 was pushed with the forefinger at a nearly-constant rate of 10 mm/min. In the respective measurements, when the measurers pushed the inner tubes 40, 140 forward until the frictional resistance is generated but stopped such ejection action in mid-course before the raised portions 60, 160 completely overpass the protrusions 70, 170 under an erroneous sensory judgement that the ejection operation was completed were recorded as "percentage of ejection action stopped in mid-course".

<Result of Measurement>

According to the measurement result, the maximum frictional resistance value for the Embodiment was about 1.0 N and the "case (%) of ejection motion stopped in mid-course" was 3.5% for the Embodiment. For the Comparative Example 1, the maximum frictional resistance value was about 2.7 N and the "case (%) of ejection motion stopped in mid-course" was 18.0% and, for the Comparative Example 2, the maximum frictional resistance value was about 3.5 N and the "case (%) of ejection motion stopped in mid-course" was 32.0%. As previously described, in the Embodiment, the raised portion 60 is heart-shaped and the width dimension thereof so gradually increases from the apex 61 (at which the frictional resistance value≈0) to the rear direction Y that the measurer may not feel a sudden generation of the frictional resistance and the maximum frictional resistance value may be limited to a relatively small level. For this reason, it is speculated that a high percentage of the measurers continued to push the inner tube 40 until the raised portion 60 overpassed the protrusion 170 without feeling that the front end 41 of the inner tube 40 was moving to the front end 31 of the outer tube 30. Meanwhile, in the Comparative Examples 1 and 2, the width dimension of the raised portion 160 is not differential between the front zone 162 and the rear zone 163 and the frictional resistance value is relatively high already at a moment of generation so that the measurers may feel a sudden generation of the frictional resistance substantially corresponding to the maximum frictional resistance value. For this reason, it is speculated that a high percentage of the measurers felt as if the front end of the inner tube 140 had already reached the front end of the outer tube 130 and stopped the operation to push out the inner tube 140 in mid-course before the raised portion 160 completely overpasses the protrusion 170.

In the light of the results obtained from the measurement conducted on the Comparative Examples 1 and 2, the case (%) of ejection motion stopped in mid-course" ranges from about 15.0 to about 25.0% when the maximum frictional resistance value ranges from about 2.5 N to about 3.0 N and when the maximum friction resistance value is 3.0 N or higher, the friction resistance value becomes too high for operation of ejection and a large segment of the measurers inevitably stops the ejection action in mid-course. In conclusion, the maximum frictional resistance value is preferably 3.0 N or less in order that most of the measurers continues to push the inner tube 40, 140 (to eject the tampon from the outer tube 30, 130 stored therein).

<Alternatives>

FIGS. 10 (*a*) through (*e*) are scale-enlarged lateral views illustrating the raised portions in several alternatives of the applicator 10 according to the present invention.

In the applicator 10 illustrated by FIG. 10(*a*) through FIG. 10(*c*), outer shapes of the raised portion 60 on the inner tube 40 are approximately spade-shape, approximately diamond-shape and approximately teardrop-shape and each of these respective raised portions 60 has the apex 61, the front zone 62 having a width dimension (surface area) gradually increasing rearward and the rear zone 63 having a width dimension (surface area) gradually decreasing rearward. Also for these raised portions 60 of these alternatives, the frictional resistance generated by slidable contact between the raised portion 60 and the protrusion 70 gradually increases from nearly a zero-resistance state as the inner tube 40 moves forward and, immediately after the frictional resistance has increased to the maximum value, the frictional resistance gradually decreases. In this way, a technical effect similar to the raised portion 60 according to the Embodiment is ensured.

The raised portion 60 illustrated in FIG. 10(*d*) has a nearly arrow-shaped contour and a frictional resistance gradually increases in the front zone 62 as the inner tube 40 moves forward but no variation of the frictional resistance occurs since the surface area in the rear zone has no variation. The raised portion 60 illustrated in FIG. 10(*e*) has a generally triangular shape and a frictional resistance gradually increases as the inner tube 40 moves forward from the apex 61 but no frictional resistance is generated immediately after the frictional resistance has reached the maximum level. Even in the raised portions 60 illustrated in FIGS. 10(*d*) and (*e*), i) the frictional resistance gradually increases from a substantially resistance-free condition at the apex 61 and ii) the surface area gradually increases from the apex to the rear so that the frictional resistance gradually increases as the inner tube 40 moves forward. For this reason, the advantageous technical effects may be ensured. According to the arrangement illustrated in FIG. 10(*e*), no frictional resistance is generated immediately after the frictional resistance has reached the maximum level and, for this reason, it is possible for the user to recognize completion of the tampon.

The constituent members of the applicator 10 are not limited to those described in the specification but the other various types of material widely used in the relevant technical field may be used without limitation unless otherwise stated.

The disclosure relating to the tampon applicator according to the present invention described above may be arranged at least as follows:

A tampon applicator comprising an outer tube having a front and a rear, openings at front and rear ends and an inner tube configured to be inserted into the rear end opening so as to be movable in a front-back direction, thereby ejecting a tampon housed within the outer tube through the front end opening, wherein: raised portion located on an exterior surface of the inner tube adjacent to the rear end thereof configured to be put in slidable contact with an interior surface of the outer tube when the front end of the inner tube moves to the front end of the exterior tube; and the raised portion has a front end, a front zone having a nearly V-shape with a width dimension gradually increasing from the apex of the front end rearward and a rear zone located behind the front zone having a width dimension gradually decreasing rearward.

The tampon applicator according to the present invention disclosed in the paragraph {0043} may include embodiments at least as described below and these embodiments may be taken in isolation or in combination.

(1) The interior surface of the outer tube partially defines a protrusion protruding inward from the interior surface and the raised portion is put in linear contact with the protrusion in a circumferential direction of the inner tube.

(2) The raised portion is located at a given distance forward from the rear end edge of the inner tube.

(3) An exterior edge of the front zone is sloped so that a height dimension gradually increases from the front to the rear.

(4) The maximum frictional resistance value generated when the raised portion is put in slidable contact with the interior surface of the outer tube is 3.0 N or less.

(5) A plurality of the raised portions are arranged on the exterior surface of the inner tube so that these raised portions may be located at intervals in a circumferential direction.

The invention claimed is:

1. A tampon applicator, comprising:
an outer tube having a front end and a rear end, a front end opening at the front end and a rear end opening at the rear end, the outer tube housing a tampon and having an insertion section on a side of the front end,
a grip section extending from the insertion section to the rear end and having a diameter smaller than a diameter of the insertion section, and
a shoulder portion located along a boundary between the insertion section and the grip section; and
an inner tube having a front end and a rear end, and configured to be inserted into the rear end opening so as to be movable in a front-rear direction, to eject the tampon housed within the outer tube through the front end opening,
wherein
raised portions are located on an exterior surface of the inner tube in a vicinity of the rear end of the inner tube,
each of the raised portions has
a front end,
a front zone having a V-shape with a width dimension gradually increasing from an apex of the front end rearwards, and
a rear zone located rearward of the front zone and having a width dimension gradually decreasing rearward, an interior surface of the grip section of the outer tube has a protrusion protruding inward from the interior surface at an edge of the rear end opening and extending circumferentially around the grip section, and the raised portions are configured to be put in slidable contact with the protrusion in a linear contact area extending in a circumferential direction of the inner tube when the front end of the inner tube moves to the front end of the outer tube.

2. The applicator according to claim 1, wherein the rear end of the inner tube has a rear end edge, and the raised portion is located at a given distance forward from the rear end edge of the inner tube.

3. The applicator according to claim 1, wherein an exterior edge of the front zone is sloped to cause a height dimension of the front zone to gradually increase from the front end of the raised portion toward the rear zone.

4. The applicator according to claim 1, wherein a maximum frictional resistance value generated when the raised portion is put in slidable contact with the protrusion at the interior surface of the outer tube is 3.0 N or less.

5. The applicator according to claim 1, wherein the raised portions are arranged on the exterior surface of the inner tube, and are located at intervals in the circumferential direction of the inner tube.

* * * * *